United States Patent [19]

Hirsch et al.

[11] Patent Number: 4,492,608
[45] Date of Patent: Jan. 8, 1985

[54] ELASTIC BAND APPLICATOR AND SHEET FOLDER

[75] Inventors: John L. Hirsch, Sheboygan Falls; Ludwig W. Freitag, Elkhart Lake, both of Wis.

[73] Assignee: Curt G. Joa, Inc., Sheboygan Falls, Wis.

[21] Appl. No.: 456,062

[22] Filed: Jan. 6, 1983

[51] Int. Cl.³ .............. B32B 31/00; B32B 31/04; B31F 5/00; B29C 19/00
[52] U.S. Cl. ................... 156/467; 156/471; 156/496; 156/554; 156/578; 156/494; 156/581; 156/264
[58] Field of Search ........... 156/461, 494, 495, 519, 156/529, 557, 581, 578, 164, 259, 264, 229, 223, 467, 471, 496, 549, 554, 465, 578, 464, 479, 357, 468; 118/411; 427/286; 226/119; 242/147 R

[56] References Cited

U.S. PATENT DOCUMENTS

| | | | |
|---|---|---|---|
| 3,298,353 | 1/1967 | Huffman | 118/411 |
| 3,553,053 | 1/1971 | Good | 156/467 |
| 3,837,972 | 9/1974 | Schuster | 156/467 |
| 3,984,272 | 10/1976 | Teed | 156/467 |
| 4,081,301 | 3/1978 | Buell | 156/549 |
| 4,240,866 | 12/1980 | Rega | 156/496 |
| 4,261,782 | 4/1981 | Teed | 156/578 |
| 4,300,967 | 11/1981 | Sigl | 156/229 |
| 4,353,762 | 10/1982 | Bouda | 156/549 |
| 4,412,881 | 11/1983 | Sigl | 156/164 |

Primary Examiner—Edward Kimlin
Assistant Examiner—Louis Falasco
Attorney, Agent, or Firm—Fuller, House & Hohenfeldt

[57] ABSTRACT

In an elastic band applicator for diapers using hot melt glue, a longitudinally tensioned moving plastic backing sheet is run over a roll that is parallel to and spaced from a stationary cylinder. A shoe deflects the central region of the sheet away from its plane at a location between the roll and cylinder. This results in the margins of the sheet beyond opposite ends of the shoe becoming loose flaps. Glue stripes are applied by means of nozzles to the sheet near its edges before the sheet encounters the shoe which has passageways for the glue stripes. Elastic bands are fed into the passageways onto the glue stripes. After passing the shoe, the margins encounter plows which turn or fold the margins over the glue stripes and bands and press the sheet against a cylinder to smooth the margin. Means are provided for retracting the sheet away from the hot nozzles if the sheet stops moving.

6 Claims, 7 Drawing Figures

U.S. Patent  Jan. 8, 1985  Sheet 1 of 2  4,492,608
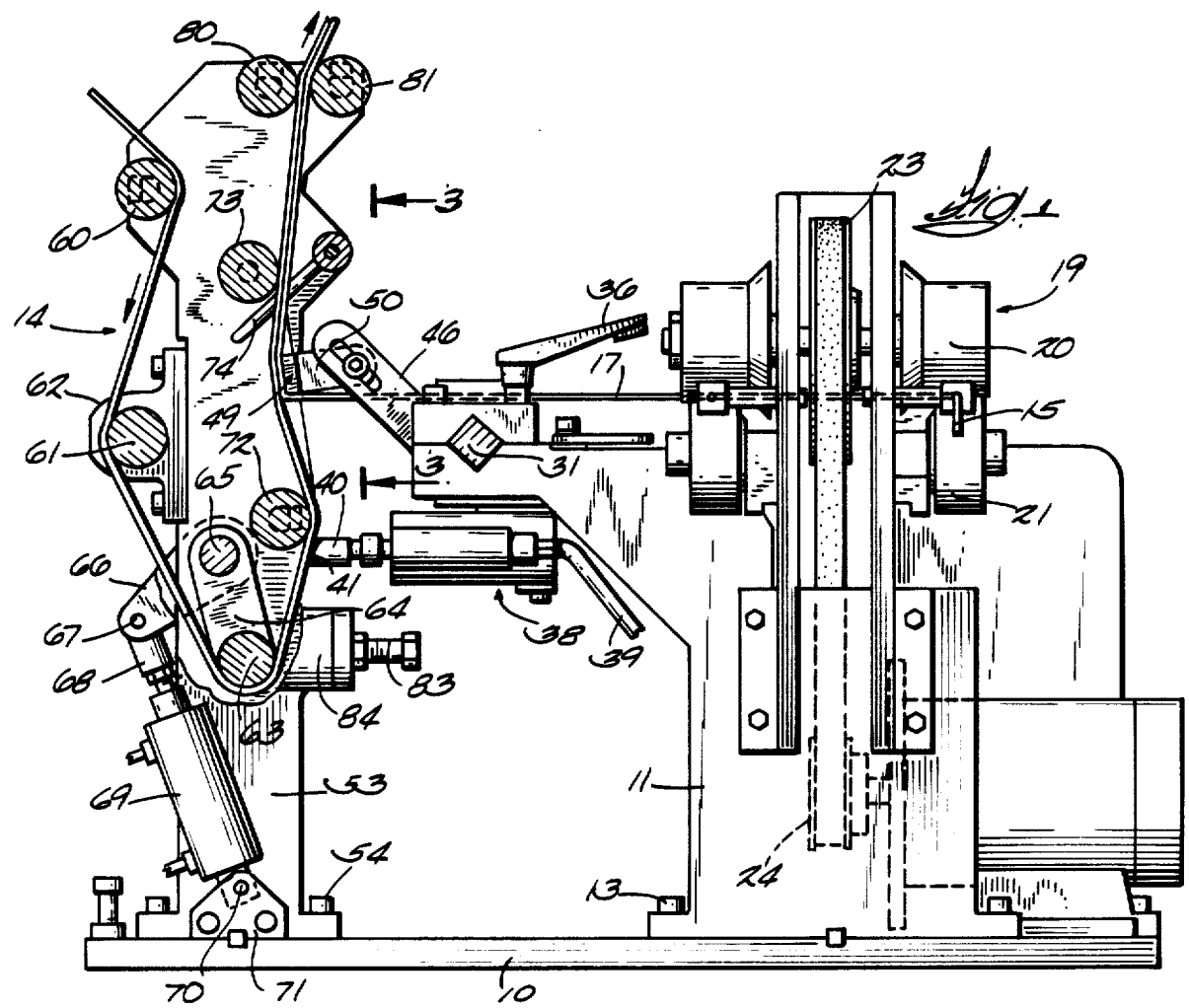
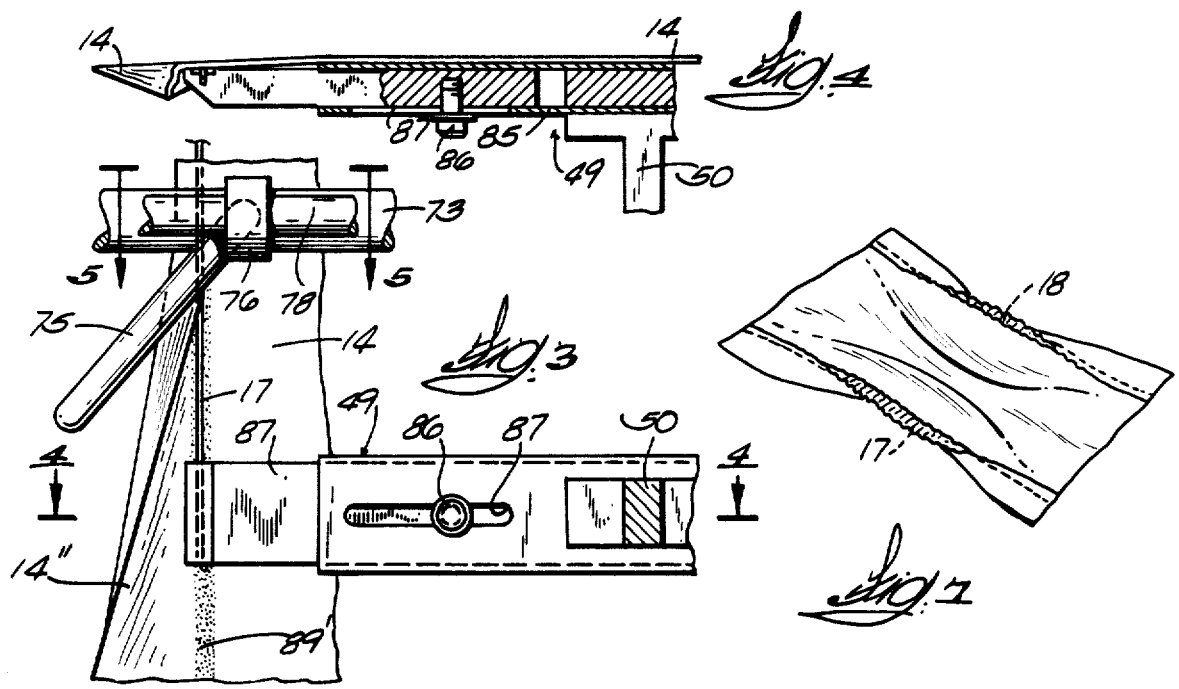

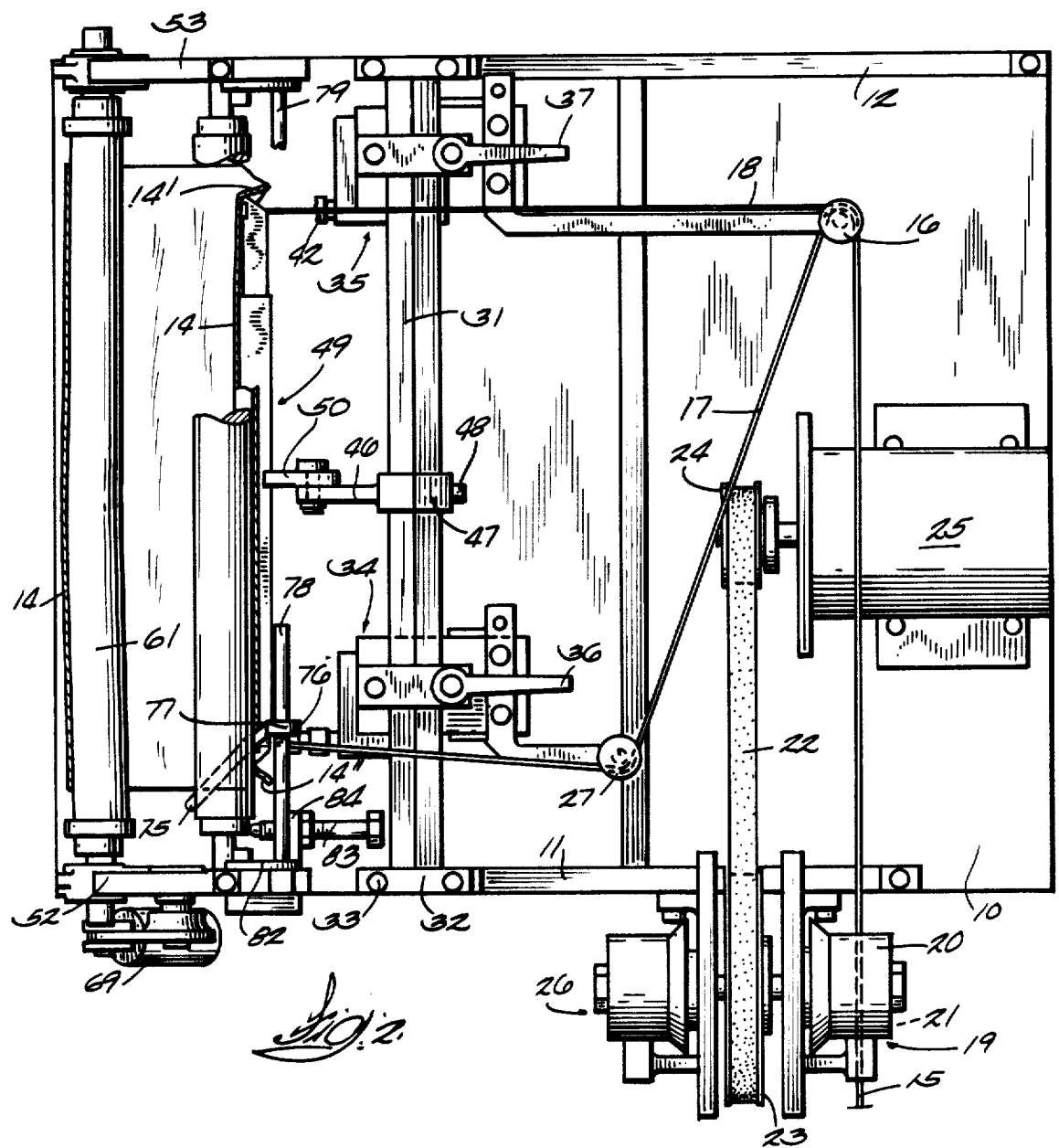
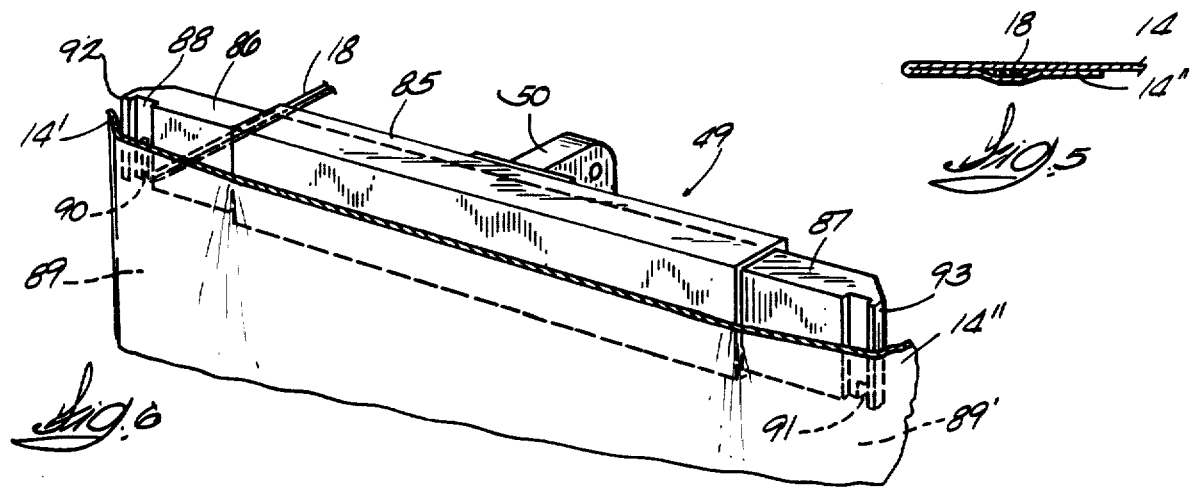

ELASTIC BAND APPLICATOR AND SHEET FOLDER

BACKGROUND OF THE INVENTION

The invention disclosed herein is a device for adhering elastic bands to a moving sheet, such as the liquid impervious backing sheet of disposable diapers, and for folding the laterally spaced apart margins of the sheet over the bands to effect adhesion.

As is well known, disposable diapers are fabricated in the form of a continuous moving web which is finally cut at regular intervals to produce individual diapers. cut at regular intervals to produce individual diapers. Typically, the web is comprised of a liquid impervious backing sheet which is commonly a plastic such as polyethylene. A layer of absorbent material such as wood fiber fluff is deposited on the sheet within the area of each diaper. A porous sheet of non-woven material is superimposed over the absorbent material and glued at its edges to the backing sheet. At some stage of the fabrication process, stretched elastic bands are applied and adhered to the backing sheet. Usually this is the first step in the process. The elastic bands contract when the individual diapers are severed and are effective to cause the edges or margins of the diaper to fit snugly against the legs and buttocks of an infant when a diaper is applied.

One type of diaper has its laterally spaced apart side margins cut away in the central region of the diaper to give it an hourglass configuration. A narrow central region thus produces less bulkiness in the crotch region of the infant. In this type of diaper, the prestretched elastic band segments are parallel with each other and extend longitudinally over the crotch region. Typically the elastic bands are about three-sixteenths of an inch wide and about one-thirty-second of an inch thick which may be considered a standard for the industry.

Another type of diaper, which is marketed as an alternative to the more expensive type just described, has no contoured crotch but is rectangular. In rectangular diapers, the elastic bands are applied to the laterally spaced apart side margins of the backing sheet and the flaps or edges of the margins beyond the bands are folded over and adhered to conceal the bands and impart the elasticity of the bands to the margins of the backing sheet for effecting a snug fit on the infant. The practice has been to score and split the three-sixteenths band longitudinally to produce two bands of half the width of the original and to apply hot melt glue directly to these narrower bands and then fold the lateral margins of the moving backing sheet over them and let the glue set. Depositing a coating of glue on opposite sides of a very thin and narrow elastic band is difficult to control properly because the delicate band has a tendency to shift out of alignment when it experiences the pressure of a glue nozzle on it. It is difficult to prevent some glue from missing the band if a spray nozzle is used. There is also a problem with depositing too little or too much glue on the band.

SUMMARY OF THE INVENTION

In accordance with the present invention, apparatus is provided for applying a stripe of glue somewhat inwardly from each edge of the backing sheet, stretching and feeding the elastic bands onto the sheet over the glue stripes, and then folding the side edges of the sheet over the band to effect gluing of the folded margin onto the body of the sheet with the elastic band captured and adhered in between. At the place where the elastic ribbon is fed in for contacting the glue stripes, a laterally extending shoe or bar is pressed against the center region of the moving sheet between and clear of the glue stripes. The pressing shoe deflects and keeps the central region of the backing sheet taut over most of the distance between its edges. The margins of the sheet beyond the ends of the bar or shoe means are then free or floppy and without tension so that they can be folded over the sheet as it progresses through the device. Immediately after the elastic band is applied, the backing sheet progresses toward laterally spaced apart folding plows which turn the margins of the sheet over the bands and the glue strips and force the sheet against a cylinder to effect adhesion.

The hot melt glue is applied as a stripe on the sheet with a slot nozzle that is in direct contact with the sheet in its marginal regions inwardly from the side edges. The nozzle is typically at a temperature that is high enough to melt or badly deform the thin plastic backing sheet if a point on the sheet remained in contact with the hot nozzle for a short time as would occur if the sheet stopped moving. When the diaper making machine in which the band applicator and folding device is incorporated is running and the sheet is moving at full speed, any point on the plastic sheet does not remain in contact with the nozzle long enough for melting to occur since heat transfer is a function of time and temperature differential. Some times the diaper making machine may be stopped several times per hour for various reasons which means that movement of the sheet past the glue nozzle stops. In accordance with the invention, means are provided to retract the sheet away from the hot glue nozzle at any time that the sheet stops moving through the band applicator and folding device.

A more detailed description of a preferred embodiment of the elastic band applicator and sheet margin folding device will now be set forth in reference to the drawings.

DESCRIPTION OF THE DRAWINGS

FIG. 1 is a side elevational view, partly in section, of the new elastic band applicator and folding device, with some parts being shown in vertical section;

FIG. 2 is a plan view of the device in FIG. 1 with some parts broken away to show what lies beneath them;

FIG. 3 is a fragmentary view looking toward the plane 3—3 in FIG. 1;

FIG. 4 is a fragmentary plan view, partially in section, of a shoe that is used for making the central region of the moving backing sheet taut while the margins of the sheet at each end of the shoe are like flaps that remain free and untensioned to permit folding the margins of the sheet over the sheet;

FIG. 5 is a cross-section of one of the marginal regions of the backing sheet after its edge has been folded over a glue stripe and the elastic band;

FIG. 6 is a perspective view of the sheet tensioning shoe, isolated from the device, for the purpose of illustrating how the backing sheet is acted upon as it passes over the shoe; and FIG. 7 is a diagrammatic view of a finished rectangularly shaped disposable diaper.

DESCRIPTION OF A PREFERRED EMBODIMENT

Considering FIGS. 1 and 2, the band applicator and folding device is comprised of a base 10 which may be mounted in a diaper manufacturing maching, not shown, near the beginning of the production line where the plastic backing sheet for the diaper web is introduced into the machine as the first step in a continuous web fabrication process. Laterally spaced apart and vertically disposed side or frame members 11 and 12 are fastened to base 10 by means of machine screws such as the one marked 13. The thin plastic backing sheet for composing a diaper is marked 14. As can be seen best in FIG. 2, the continuous elastic band is marked 15 where it is input to the device. At the input, by way of example and not limitation, the elastic band has a width, typically, of three-sixteenths of an inch and is scored longitudinally along its center. The band runs toward a post 16 where it is torn on its score line and divided into two separate halfwidth bands 17 and 18 in the illustrated embodiment. Undivided and scored band 15 is fed into the band applicator and folding device through a feed roll mechanism which is generally designated by the reference numeral 19. In the feed roll mechanism, the band is gripped between upper and lower rollers 20 and 21 which are driven rotationally by a belt 22 that runs on a driven pulley 23 and a driving pulley 24. Pulley 24 is mounted on the shaft of a motor 25 whose speed can be adjusted but is held constant during a run. The feed roll mechanism 19 is of a known type and need not be described in any detail. It is sufficient to recognize that it allows for feeding the elastic band into the applicator and folding device at a controlled rate. The feed rolls 19 are rotated at a peripheral speed that is a percentage of the linear speed of the plastic backing sheet 14, thus stretching the elastic bands before they become adhered to the sheet.

The feed roll mechanism is symmetrical in that it is provided with another pair of rollers 26 for feeding in an elastic band. In some cases it may be convenient to separate the scored band into two parts before going through the feed roll mechanism. In such case, the part 17 which now comes off of pulley 16 could run directly from feed roll 26 to another post 27 and then go into the apparatus for depositing the band on the diaper. backing sheet. The arrangement also permits feeding in two unscored elastic bands of any width if that is desired in a particular diaper style.

A square cross-section bar 31 extends laterally across the space between upstanding stationary side members 11 and 12. Bar 31 is secured to the side members by clamps, such as the one marked 32 in FIG. 2, and the clamps are secured with machine screws 33. A pair of carriages 34 and 35 are movable laterally on bar 31 and can be clamped so they remain in a fixed position on the bar by turning some clamping screw handles 36 and 37 in the appropriate direction to effect clamping. Carriages 34 and 35 support glue guns such as the one which is shown in profile in FIG. 1 and is designated generally by the numeral 38. An infeed tube for hot melted glue is marked 39. The glue applicator gun nozzle 40 is a so-called slot nozzle which has a slot 41 in its tip. By way of example, and not limitation, slot 41 may have a length in the direction perpendicular to the plane of the drawing in FIG. 1 of about three-sixteenths of an inch and a width of about 0.010 inch. Thus, this particular nozzle tip will deposit on backing sheet 14 a stripe of hot melt glue having a width of about three-sixteenths of an inch on moving plastic diaper web backing sheet 14 as the sheet moves through the band applicator and folding apparatus. The glue discharge nozzle of the gun on carriage 35 is shown broken away for the sake of clarity and is marked 42 as can be seen in FIG. 2. The nozzles apply a stripe of glue on the margins or a small lateral distance inwardly from the edges of the backing sheet 14 and the stripe is slightly wider than the elastic band. Thus, when the edges of the backing sheet are folded over, the edges are also glued.

An arm 46 is also mounted on cross-bar 31. The arm has an opencentered portion 47 which permits it to be slid on cross-bar 31 and to be secured in any desired lateral location by tightening a machine screw 48 against the bar. A plastic sheet stretching and depression forming shoe assembly 49 is supported from bar 46. Shoe assembly 49 has a rigid arm 50 extending from it and it makes an angularly adjustable connection with arm 46 by means of a bolt 51 that can be loosened and tightened to set the angle of the shoe assembly 49. A perspective view of shoe assembly 49 appears in FIG. 6. Its function will be discussed shortly hereinafter.

Referring to FIGS. 1 and 2 again, one may see that there are two upstanding frame members or columns 52 and 53 mounted to the base 10 with machine screws such as the one marked 54. A plurality of rolls and non-rotating cylinders span between columns for defining the pathway which longitudinally tensioned plastic backing sheet 14 must follow through the glue applicator and sheet folding device. The first cylindrical roll encountered by the incoming sheet 14 is marked 60. Another is a non-rotating Mount Hope type roll marked 61 which is arced or crowned in its central region and serves to smooth out the plastic sheet. Roll 61 is clamped in block 62. Next downstream from roll 61 there is a roll 63 that is mounted for rotation on a pair of links one of which is shown and marked 64. Links 64 are fastened to a shaft 65 which is mounted for rotation in columns 52 and 53. Shaft 65 has another link 66 fastened to it. Link 66 is pivotally connected at 67 to the ram 68 of a pneumatic cylinder 69. It will be evident that when ram 68 of pneumatic cylinder 69 is extended, shaft 65 will rotate clockwise and swing roller 63 on link 64 to the left, thereby withdrawing plastic sheet 14 from contact with the glue applicator nozzle tip 41. Any time the diaper making machine is stopped, movement of backing sheet 14 also stops, of course. A solenoid valve, not shown, is operative to feed pressurized air to pneumatic cylinder 65 coincident with stoppage of the diaper making machine to thereby retract backing sheet 14 out of contact with the glue applicator nozzle tips. Pneumatic cylinder 69 oscillates about a pivot 70 on a bracket 71 which is mounted to base 10 of the elastic band applicator and sheet folding device. Bolts 83 are mounted in brackets 84. Bolts 83 act as stops for the swingable roll 63 and are used for controlling the amount of pressure between sheet 14 and the glue nozzles 41 and 42.

There is another sheet supporting and guiding roll 72 journaled for rotation on side columns 52 and 53. Roll 72 keeps the sheet 14 in contact with the pair of glue nozzle tips 41 which are slightly downstream from roll 72. Roll 72 also participates in the process of creating a laterally extending depression or dip in the central region of the tensioned sheet 14 as a result of the shoe assembly 49 pressing against the sheet as will be elaborated shortly hereinafter.

There is a non-rotating roll or cylinder 73 upstream from the shoe assembly 49. This cylinder is adjacent a folding rod 74 that acts as a plow to fold the outer margins or edges of the backing sheet 14 over the elastic rubber bands after the sheet has passed beyond the shoe assembly 49. One of the plow or folding rods 74 is visible in FIG. 1 and the other 75 is visible in FIG. 2. Typical rod 75 in FIG. 2 extends from a collar 76 in which there is a screw 77 for allowing the sheet edge folding rod to be adjusted to any lateral position and at any angle with respect to a fixed shaft 78 on which typical folding rod 75 is mounted. The shaft 79 for supporting rod 74 is broken away in FIG. 2. However, it should be recognized that both folding rods 74 and 75 are normally in use and are similarly angulated for doing the sheet margin folding operation. Folding rods 74 and 75 are not only adjustable angularly and laterally on shafts 78 and 79 but they are also adjustable vertically since they are mounted on vertically movable members such as the one marked 82 in FIG. 2. The folding rods turn over the edges of the moving sheet 14 and press them against the stationary cylinder.

Also spanning between columns 52 and 53 are the uppermost pair of guide rolls 80 and 81 which are the sheet exit rollers of the applicator and folding device. It will be understood that after the elastic bands are applied to the sheet and its margins folded and glued over the bands, the longitudinally tensioned sheet goes downstream out of guide rolls 80 and 81 to the next station in a diaper making machine, not shown, wherein parallel longitudinal glue stripes, not shown, may be applied for holding the absorbent fluff that goes to compose each diaper.

Refer now to FIG. 6 where the sheet 14 depressing and folding bar assembly 49 is isolated and shown in detail. In FIG. 6 and in FIG. 4, too, one may see that the shoe assembly 49 is comprised of a hollow tubular base member 85 which has an interior that is rectangular in cross-section. The base member could have other forms, for instance, it could be a channel member. Independent bar elements 86 and 87 are adjustable laterally within tubular member 85. As shown in FIG. 4, bar elements 86 and 87 can be clamped in fixed position within tubular base member 85 with screws such as the one marked 86 that pass through slots 87 in the back of the base member 85. Typical laterally adjustable bar element 86 has a longitudinally extending channel passageway 88. This passageway is slightly wider than the width of the hot melt glue stripe that is deposited by the glue nozzle tips 41. A typical glue stripe is marked 89 and shown in dashed lines in FIG. 6. Since the passageways 88 are wider than the glue stripes 89 the glue does not get smeared onto the bar elements 86 and 87 of the shoe assembly 49. The bar elements 86 and 87 also have notches 90 and 91, respectively, in their lower edges. These notches act as input guides for the elastic rubber band which is typified by band 18 in FIG. 6. In FIG. 6, one may see that the lateral length of the shoe assembly 49 between the ends or extremities 92 and 93 of the bar elements 86 and 87 is less than the width of backing sheet 14 so there remains margins 14' and 14" on the sheet 14 which are loose and untensioned flaps that are capable of being folded over the body of sheet 14 near its edges. These flaps or loose margins 14' and 14" result from the fact that shoe assembly 49 presses the central region of the sheet to cause a depression or dip in sheet 14 which is very taut and offset from the normal plane of the sheet as can be seen in FIG. 6. As is evident in FIG. 1, when shoe 49 presses against the central region of sheet 14, the sheet is backstopped by roll 72 and stationary cylinder 73 as well. The sheet is always under longitudinal tension as it passes through the device. The sheet 14 also has a longitudinal velocity greater than the velocity at which the rubber bands are fed in so that the bands are pre-stretched before they become glued. After a region of the backing sheet passes over the face of the shoe 49, the floppy or free margins of the sheet 14' and 14" are completely turned over by the plow rods 74 and 75 and the force of the plow rods presses the margins against stationary cylinder 73.

FIG. 3 shows the sheet deflection and margin folding process in more detail. The glue stripe 89' has been deposited by nozzle tip 41 and backing sheet 14 is moving upwardly or in the downstream direction. Elastic band 17 is being fed in from the bottom of the passageway on the front of end bar 87 of shoe 49. The stretched band 17 is moving along with the sheet 14. The central region of the sheet 14 is deflected and stressed, thereby making margin 14" loose or unstressed. Margin 14" is in contact with and being deflected by angulated rod or plow 75 such that the margin becomes folded over the glue stripe. Because of the plow rod 75 being angulated, the margins of the moving sheet yields toward stationary cylinder 73 where the margin becomes compressed against the body of sheet 14 so the elastic band becomes concealed under the folded margin.

FIG. 5 shows a section through the margin of the sheet after the quick-setting hot melt glue has been set such that the folded over margin of the sheet 14 is attached to the main body of the sheet and an elastic band is fastened in pre-stretched condition to the main and marginal parts of the sheet.

FIG. 7 shows an individual disposable diaper whose fabrication has been completed in other stations, not shown, in the continuous web diaper manufacturing line. Note that when the diaper is severed from the continuous web, elastic bands 17 and 18 become unstretched which causes a slight ruffling in the backing sheet 14 edges. When the diaper is put on the infant, of course, the bands stretch out again and provide a contractile force that causes the margin of the diaper to fit snugly and conformingly against the infant's body.

Although a preferred embodiment of the new glue applicator and folding device has been described in detail, such description is intended to be illustrative rather than limiting, for the invention can be variously modified and is to be limited in scope only by interpretation of the claims which follow.

I claim:

1. Apparatus for applying elastic bands to the laterally spaced apart margins of a longitudinally moving sheet, such as a sheet that is part of a diaper, comprising:

first and second parallel cylindrical members spaced apart in the longitudinal direction of the moving sheet, the second cylindrical member being located downstream of the first one and the sheet running in the same plane on the members under longitudinal tension, shoe means extending laterally of the sheet and having a length from end-to-end that is less than the width of said sheet, said shoe means having a side for interfacing with the sheet and being positioned between the first and second cylindrical members for pressing against the sheet to deflect laterally extending central region of the sheet and put said region under lateral tension while letting opposite laterally spaced apart margins of the sheet beyond the ends of the shoe means remain free and untensioned, nozzle means preceding said shoe means to apply longitudinally extending stripes of glue that are wider than the elastic bands to be attached to said margins of the sheet, said side of the shoe means interfacing with said sheet having passageways wider than the glue stripes through which said glue stripes pass and into which said elastic bands, respectively, of lesser width than the glue stripes are fed onto said sheet over the glue stripes, and folding means next downstream from said shoe means, said folding means being constructed and arranged for folding said sheet margins over said glue stripes on the sheet to effect adhesion of the margins to the sheet with the glue stripe margins remaining on each side of the bands.

2. The apparatus as in claim 1 wherein said folding means comprises:

a folding element extending at an angle relative to the plane of the sheet for the margin of the sheet to run over said element and follow its angle for being folded and pressed toward and against said second cylindrical member to thereby secure the overlapping margin.

3. The apparatus as in any of claims 1 or 2 including: means operative to retract said sheet away from said nozzle when movement of said sheet stops.

4. The apparatus as in any of claims 1 or 2 including:
a roll upstream from said nozzle over which roll said sheet runs, means supporting said roll for swinging to one position wherein said roll will urge the sheet against the nozzles and to another position wherein said roll will hold said sheet away from said nozzles, and means operating substantially coincidentially with said sheet stopping to cause said roll to swing from said one position to said other position.

5. The apparatus as in any of claims 1 or 2 wherein said shoe means comprises:

a base member for extending laterally over part of the distance between the laterally spaced apart margins of said sheet, bar means and means for adjusting and fixing said bar means to said base member for said bar means to extend laterally outwardly and in opposite directions such that the distance between their outer ends substantially determines the width of said central region of the sheet that is deflected, said bar means having near their ends on the sides thereof which interface with the sheet the aforementioned passageways through which said glue stripe passes.

6. The apparatus in any of claims 1 or 2 including:
means for feeding said elastic bands toward said sheet at a linear velocity that is less than the velocity of the sheet, to thereby cause said bands to stretch as they are being fed for being glued to the sheet.

* * * * *